US00PP15248P2

(12) United States Plant Patent
Whetman

(10) Patent No.: US PP15,248 P2
(45) Date of Patent: Oct. 19, 2004

(54) ***DIANTHUS* PLANT NAMED 'DEVON OCTAVIA'**

(50) Latin Name: *Dianthus×hybrida*
Varietal Denomination: Devon Octavia

(76) Inventor: John Whetman, Deer Park Farm, Chudleigh, Devon TQ13 ONM (GB)

( * ) Notice: Subject to any disclaimer, the term of this patent is extended or adjusted under 35 U.S.C. 154(b) by 0 days.

(21) Appl. No.: 10/676,192

(22) Filed: Sep. 30, 2003

(51) Int. Cl.[7] ..... A01H 5/00
(52) U.S. Cl. ..... Plt./273
(58) Field of Search ..... Plt./273

*Primary Examiner*—Anne Marie Grunberg
*Assistant Examiner*—Annette H Para

(57) ABSTRACT

A new cultivar of *Dianthus* plant named 'Devon Octavia' that is characterized by compact mounding habit, medium-green foliage and pink and red flowers that bloom from April to October. In combination these traits set 'Devon Octavia' apart from all other existing varieties of *Dianthus* known to the inventor.

2 Drawing Sheets

Genus: *Dianthus.*
Species: *xhybrida.*
Denomination: 'Devon Octavia'.

BACKGROUND OF THE INVENTION

The present invention relates to a new and distinct cultivar of carnation that is grown for use as an ornamental container plant. The new cultivar is known botanically as *Dianthus xhybrida* and will be referred to hereinafter by the cultivar name 'Devon Octavia'.

'Devon Octavia' is a hybrid plant that is the product of a breeding program started by the inventor in 1980. The breeding program is not federally funded and is on going, conducted in cultivated area of Houndspool, Dawlish, Devon, United Kingdom. The primary focus of the breeding program is to produce new cultivars of carnations that exhibit unique growth habit.

'Devon Octavia' was selected in 2000, by the inventor, from a large group of open pollinated seedlings. The exact parents are unknown. The female parent plant is presumed to be an unidentified cultivar of *Dianthus* and the male parent is presumed to be an unidentified cultivar of *Dianthus*. There are no close comparison plants known to the inventor.

Asexual reproduction of the new cultivar 'Devon Octavia' was first accomplished by the inventor in 2000 in a cultivated area of Houndspool, United Kingdom. The method of sexual propagation used was vegetative stem cuttings. Since that time the characteristics of the new cultivar have been determined stable and are reproduced true to type in successive generations by vegetative propagation.

SUMMARY OF THE INVENTION

The following traits have been repeatedly observed and represent the characteristics of the new *Dianthus* cultivar 'Devon Octavia'. These traits in combination distinguish this cultivar from all other commercial varieties known to the inventor. 'Devon Octavia' has not been tested under all possible conditions and phenotypic differences may be observed with variations in environmental, climatic and cultural conditions without however any variation in genotype.

1. *Dianthus* 'Devon Octavia' exhibits a compact mounding growth habit.

2. *Dianthus* 'Devon Octavia' exhibits pink and red flowers.
3. *Dianthus* 'Devon Octavia' exhibits medium-green foliage.
4. *Dianthus* 'Devon Octavia' is 25–30 cm. in height and 15–20 cm in width.
5. *Dianthus* 'Devon Octavia' is an evergreen perennial herb.
6. *Dianthus* 'Devon Octavia' blooms from April to October.
7. *Dianthus* 'Devon Octavia' is hardy to minus 15° Centigrade.

BRIEF DESCRIPTION OF THE DRAWINGS

The accompanying color drawings illustrate the overall appearance of the new *Dianthus* variety 'Devon Octavia' showing colors as true as it is reasonably possible to obtain in colored reproductions of this type. Colors in the drawings may differ from the color values cited in the detailed botanical description, which accurately describe the actual colors of the new variety 'Devon Octavia'.

The drawing on sheet 1 illustrates a 4-month-old plant in a 1.0-litre container.

The drawing on sheet 2 is a close-up of a typical flowers. The plants in the drawings were grown from 3 cm-plugs in an open-sided polythene structure in Devon, United Kingdom. No chemicals were used to treat plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Octavia'. Data was collected from plants grown in 1.5-litre containers grown under glass in Houndspool, United Kingdom. The color determinations are in accordance with the 2002 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus* 'Devon Octavia'.
Species: *xhybrida.*
Common name: Devon *dianthus.*
Commercial classification: Hybrid.
Type: Perennial herb.
Use: Ornamental plant for small pots and containers.
Parentage: 'Devon Octavia' is a hybrid plant that resulted from the open pollination of unknown cultivars of *Dianthus*. The exact parents are unknown:
*Female parent plant.*—Presumed to be an unidentified cultivar of *Dianthus.*
*Male parent plant.*—Presumed to be an unidentified cultivar of *Dianthus.*
Plant description:
*Bloom period.*—April to October.
*Plant habit.*—Compact mounding habit.
*Plant height.*—25–30 cm. in height.
*Plant width.*—15–20 cm. in width.
*Plant hardiness.*—Hardy to minus 15° Centigrade.
*Type.*—Perennial herb.
*Root system.*—Fibrous.
*Propagation.*—Propagation is accomplished using vegetative stem cuttings.
*Cultural requirements.*—Plant in full sun, well-drained and moderately fertile soil and keep well fertilized and watered.
*Diseases and Pests.*—Susceptible to known *Dianthus* pests and disease but no other susceptibilities to pests or disease are known to the inventor.
*Time required to produce a rooted cutting.*—2 weeks are needed to develop roots on an initial cutting, and 5 weeks to produce a plug plant.
*Temperature recommended for rooting.*—The air temperature needed is a minimum of 15° Centigrade air temperature and base heat of 21° Centigrade.
*Crop time.*—4–7 months is needed to produce a finished 1.5-litre container size from a well-rooted cutting.
Stem:
*Shape.*—Cylindrical.
*Stem.*—25–30 cm. in length and 4 mm. in diameter.
*Stem surface.*—Glabrous and glaucous.
*Stem color.*—N138A.
*Branching.*—Numerous basal breaks.
*Internode length.*—15–60 mm. between nodes.
*Node dimensions.*—2 mm. in diameter and 5 mm. in length.
*Node color.*—144C.
Foliage:
*Type.*—Evergreen.
*Shape.*—Lanceolate.
*Division.*—Simple.
*Apex.*—Acute.
*Base.*—Decurrent.
*Venation.*—Not prominent.
*Margins.*—Entire.
*Attachment.*—Sheathing.
*Arrangement.*—Opposite and spiraling on stem.
*Surfaces* (*adaxial and abaxial*).—Glaucous.
*Leaf dimensions.*—90 mm. in length and 7 mm. in width.
*Leaf color* (*adaxial surfaces*).—N138A.
*Leaf color* (*abaxial surfaces*).—137C.
*Stipulates.*—Absent.
*Fragrance.*—Medium.
Flowers:
*Inflorescence.*—Raceme with branches.
*Flower type.*—Double and symmetrical.
*Flower shape.*—Salviform.
*Flower dimensions* (*including calyx*).—35 mm. in length and 40–45 mm. in diameter.
*Bud color.*—138B.
*Anthocyanin.*—Absent.
*Bud dimensions.*—20–25 mm. in length and 6–8 mm. in width.
*Bud shape.*—Cylindrical.
*Petals.*—Persistent, apopetalous, overlapping.
*Petal number.*—15 in number and 10 petaloid stamens.
*Petal dimensions.*—20 mm. in length and 35 mm. in width.
*Petal margin.*—Slightly dentate (toothed 1 mm deep).
*Petal shape.*—Obdeltoid.
*Petal color* (*adaxial surface*).—Colors 55D, 155C, and 149D are each individually present on individual petal.
*Petal color* (*abaxial surface*).—Colors 55B, 55C, 46A, and 149D are each individually present on individual petal.
*Petal surfaces* (*adaxial and abaxial*)—. Glabrous.
*Calyx dimensions.*—8 mm. in width and 20 mm. in length.
*Sepal color* (*adaxial surfaces*).—N138A.
*Sepal color* (*abaxial surfaces*).—N138A.
*Anthocyanin.*—Absent.
*Sepal number.*—5 in number.
*Fused or unfused.*—Fused.
*Epicalyx.*—4 bracts in number (2 larger and 2 smaller).
*Bract dimensions* (*larger*).—5 mm. in diameter and 6 mm. in length.
*Bract dimensions* (*smaller*).—4 mm. in diameter and 6 mm. in length.
*Epicalyx color* (*adaxial surfaces*).—N138A.
*Epicalyx color* (*abaxial surfaces*).—N138A.
*Anthocyanin.*—Absent.
*Peduncle dimensions.*—15–30 mm. and 1 mm. in diameter.
*Peduncle color.*—138B.
*Fragrance.*—Medium fragrance.
*Lastingness of flower.*—Each individual flower lasts 10 days at 20° Centigrade.
*Stipules.*—2 in number.
*Stipule dimensions.*—8 mm. in length and 2 mm. in width.
*Stipule color.*—N138A.
*Anthocyanin.*—Absent.
Reproductive organs:
*Stamens.*—Number varies from 0–5 on individual flowers.
*Stamen color.*—155C.
*Stamen dimensions.*—10 mm. in length and 0.5 mm. in diameter.
*Anther.*—Absent.
*Styles.*—Two in number.
*Style color.*—155C.
*Style dimensions.*—23 mm. in length and 1 mm. in diameter.
*Stigma.*—Single stigma.
*Color of stigma.*—155C.
*Stigma height.*—5 mm. above petals in maturity.
*Ovary position.*—Superior.
*Ovary dimensions.*—8 mm. in length and 5 mm. in diameter.
*Ovary shape.*—Spindle shaped.
*Ovary color.*—Apical half is N144D and basal half is 145D.
Seed: No seed has been observed to date.

I claim:

1. A new and distinct cultivar of *Dianthus* plant named 'Devon Octavia' as described and illustrated herein.

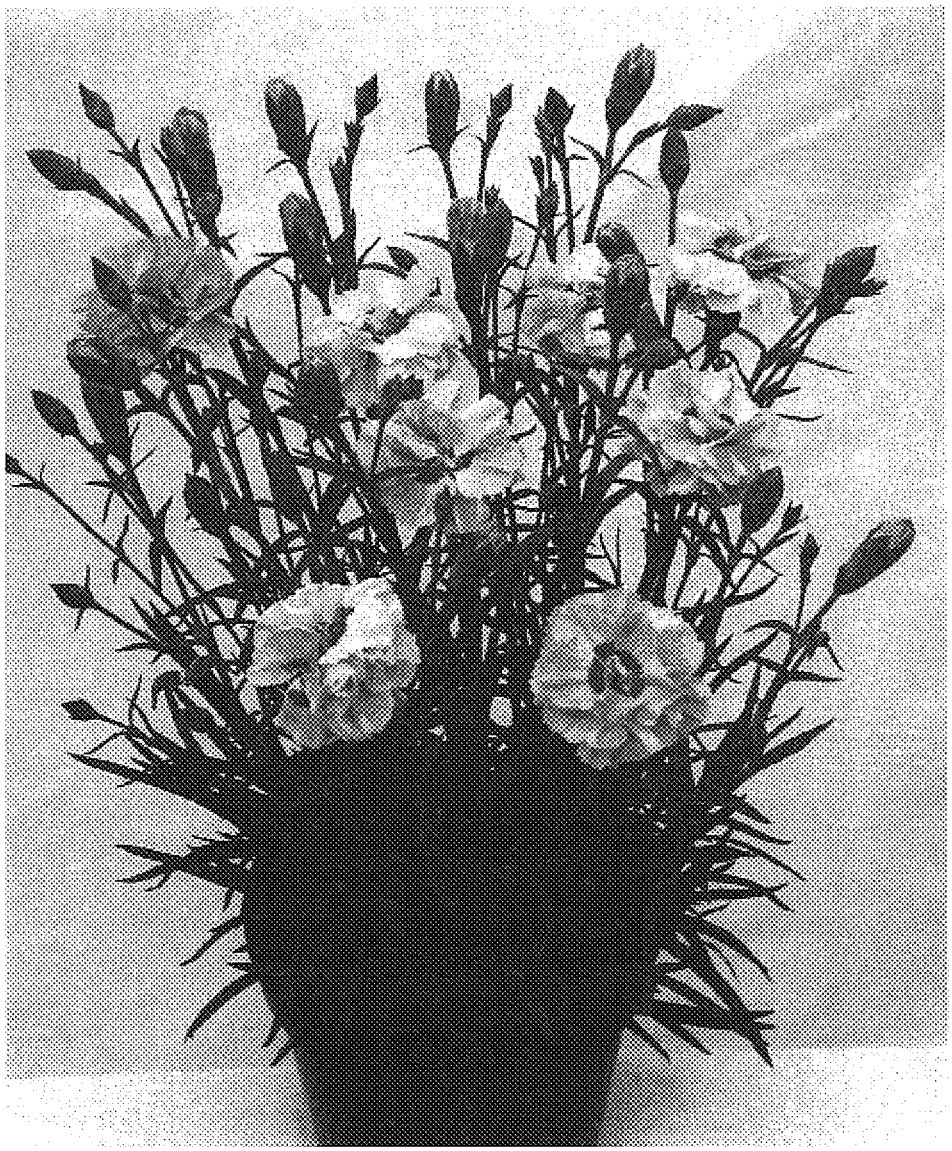

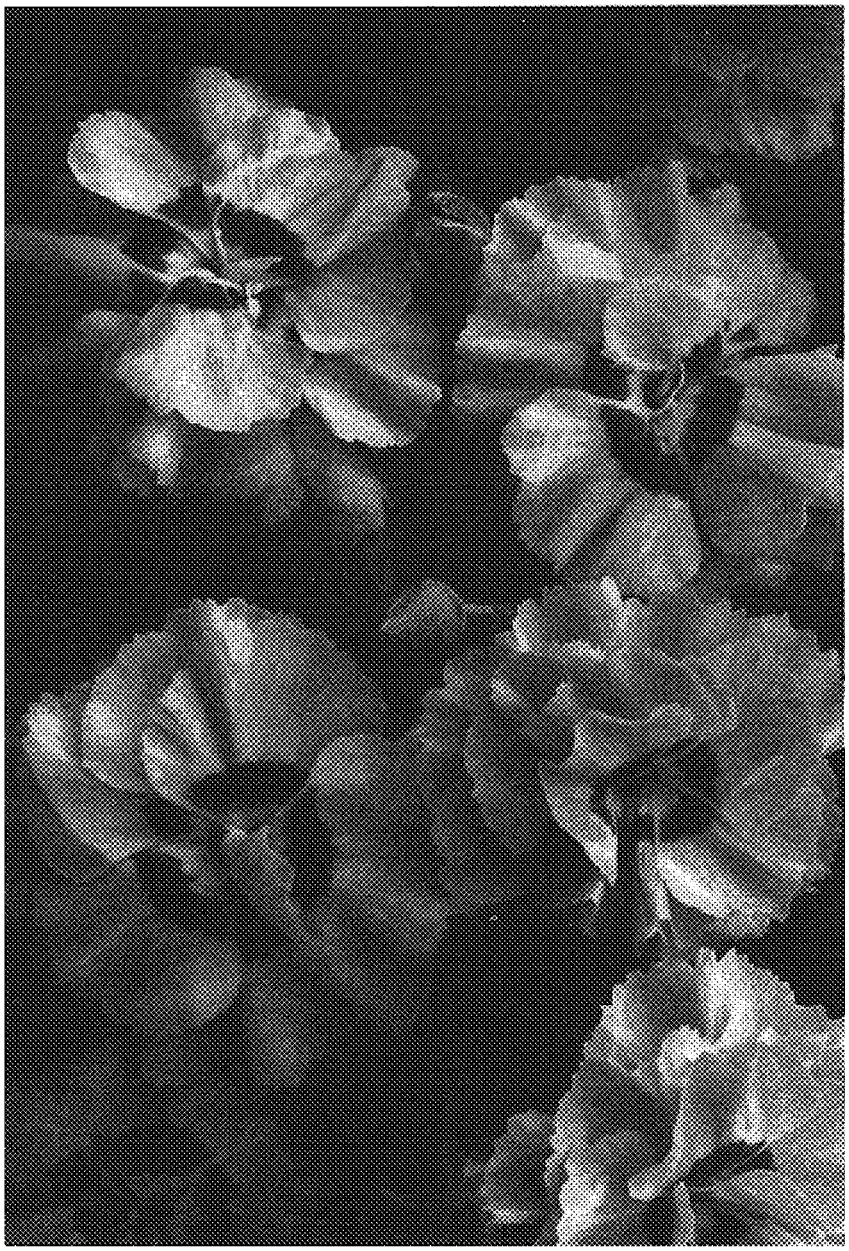

* * * * *